(12) United States Patent
Hight (10) Patent No.: US 11,344,904 B2
(45) Date of Patent: May 31, 2022

(54) STORAGE CONTAINER AND DISPENSER (71) Applicant: Myra Hight, South Lake Tahoe, CA (US)

(72) Inventor: Myra Hight, South Lake Tahoe, CA (US)

( * ) Notice: Subject to any disclaimer, the term of this patent is extended or adjusted under 35 U.S.C. 154(b) by 9 days.

(21) Appl. No.: 16/794,178

(22) Filed: Feb. 18, 2020

(65) Prior Publication Data
US 2020/0261935 A1 Aug. 20, 2020

Related U.S. Application Data (60) Provisional application No. 62/807,358, filed on Feb. 19, 2019.

(51) Int. Cl.
*B05B 11/02* (2006.01)
*B05B 11/00* (2006.01)

(52) U.S. Cl.
CPC .......... *B05B 11/02* (2013.01); *B05B 11/0089* (2013.01)

(58) Field of Classification Search
CPC ..... B05B 11/02; B05B 11/0089; B65D 69/00; B65D 81/26; B65D 1/06; B65D 5/726; B65D 83/0005; A61M 5/002; A61M 5/3202; A61M 5/50; A61M 3/0266; A61M 2209/06; A61M 5/315; A61B 2017/00362
USPC ........ 222/179.5; 53/158, 444, 452; 604/192, 604/197, 263, 403; 206/363–370, 433, 206/429, 521–524, 591–594
See application file for complete search history.

(56) References Cited

U.S. PATENT DOCUMENTS

| | | | | |
|---|---|---|---|---|
| 1,581,341 A | * | 4/1926 | Guinness ............. | A61M 5/002 206/210 |
| 1,924,205 A | * | 8/1933 | Everett, Jr. ........ | B65D 83/0005 222/386 |
| 2,270,935 A | * | 1/1942 | Doering ............ | B65D 83/0005 426/115 |
| 2,515,956 A | | 7/1950 | Greenberg | |
| 2,585,602 A | * | 2/1952 | Turner ................... | A01K 97/08 220/796 |
| 2,602,567 A | * | 7/1952 | Goon ................. | B65D 83/0005 220/578 |
| 3,273,760 A | * | 9/1966 | Frankenberg ...... | B65D 83/0005 222/386 |
| 3,545,607 A | * | 12/1970 | Keller ..................... | A61M 5/28 206/365 |
| 3,674,181 A | | 7/1972 | Marks et al. | |
| 3,746,155 A | * | 7/1973 | Seeley ................... | B65D 75/32 206/365 |

(Continued)

*Primary Examiner* — Benjamin R Shaw
(74) *Attorney, Agent, or Firm* — Ariel S. Bentolila; Bay Area IP Group, LLC (57) ABSTRACT

A viscous concentrate dispensing device includes a storage container tube configured to hold a viscous concentrate, a first cap configured to fit over a first end of the storage container tube, and a second cap configured to fit over a second end of the storage container tube. The first and second cap hold the storage container tube in place for storage and seal the viscous concentrate within the storage container tube. A plunger is configured to fit in the first cap and the second cap and hold the plunger in place for storage. A seal is disposed within the storage container tube for extruding the viscous concentrate when a force is applied with the plunger to depress the seal.

20 Claims, 5 Drawing Sheets

(56) References Cited

U.S. PATENT DOCUMENTS

| | | | | |
|---|---|---|---|---|
| 3,869,062 | A * | 3/1975 | Jaeschke | A61M 5/002 206/229 |
| 4,011,868 | A * | 3/1977 | Friend | A61M 5/31511 604/194 |
| 4,390,016 | A * | 6/1983 | Riess | A61M 5/002 604/194 |
| 4,403,707 | A | 9/1983 | Connor | |
| 4,581,023 | A * | 4/1986 | Kuntz | A61M 5/24 604/234 |
| 5,067,947 | A * | 11/1991 | Volk | A61M 5/50 604/201 |
| 5,421,488 | A * | 6/1995 | Ehrbar | B65D 1/06 215/2 |
| 5,445,523 | A * | 8/1995 | Fischer | B05C 17/00593 433/90 |
| 5,549,594 | A * | 8/1996 | Brunken | A61B 1/00137 606/1 |
| 5,554,151 | A * | 9/1996 | Hinchliffe | A61B 10/0096 606/1 |
| 5,681,317 | A * | 10/1997 | Caldarise | A61B 17/8825 604/218 |
| 5,806,708 | A * | 9/1998 | Schwab | A45C 11/008 220/378 |
| 6,527,115 | B2 * | 3/2003 | Rabiner | B65D 43/20 206/363 |
| 6,585,690 | B1 * | 7/2003 | Hoeck | A61M 5/3234 604/110 |
| 6,913,592 | B2 * | 7/2005 | Parsons | A61M 5/30 604/218 |
| 7,141,036 | B2 * | 11/2006 | Berman | A61M 31/00 604/60 |
| 7,632,244 | B2 * | 12/2009 | Buehler | A61M 5/50 206/726 |
| 8,454,558 | B2 * | 6/2013 | Jessop | A61C 5/62 604/87 |
| 8,657,793 | B2 * | 2/2014 | Pellegrini | A61M 5/315 604/187 |
| 9,333,288 | B2 * | 5/2016 | Hilliard | B65D 81/266 |
| 9,821,119 | B2 * | 11/2017 | Felsovalyi | A61M 5/31511 |
| 10,286,142 | B2 * | 5/2019 | Amarchinta | A61M 5/002 |
| 10,322,861 | B2 * | 6/2019 | McArdle | B65D 75/366 |
| 2006/0229568 | A1 * | 10/2006 | Koopman | A61M 5/31511 604/187 |
| 2006/0260276 | A1 * | 11/2006 | Baldwin | B65B 3/006 53/137.2 |
| 2007/0090081 | A1 * | 4/2007 | Briscoe | A47G 19/2272 215/307 |
| 2008/0067104 | A1 * | 3/2008 | Curnow | A61B 50/30 206/586 |
| 2009/0261098 | A1 * | 10/2009 | Coffey | B65D 1/06 220/200 |
| 2010/0187246 | A1 * | 7/2010 | Miura | B65D 23/106 220/771 |
| 2011/0046603 | A1 * | 2/2011 | Felsovalyi | A61M 5/31511 604/506 |
| 2012/0150140 | A1 * | 6/2012 | Ginzburg | A61J 1/1418 604/500 |
| 2013/0081974 | A1 * | 4/2013 | Hilliard | A61M 5/31511 206/571 |
| 2014/0311940 | A1 * | 10/2014 | Braveman | B65D 1/10 206/524.6 |
| 2015/0093477 | A1 * | 4/2015 | McNamara | B65D 1/0223 426/112 |
| 2015/0129447 | A1 * | 5/2015 | Tremblay | B65D 85/30 206/433 |
| 2015/0283030 | A1 * | 10/2015 | Skufca | A61J 1/2013 604/413 |
| 2016/0376075 | A1 * | 12/2016 | Bacher | B65D 51/145 215/260 |
| 2017/0158381 | A1 * | 6/2017 | Holland | B65D 35/46 |
| 2018/0086543 | A1 * | 3/2018 | Van Why | B65D 83/0022 |

* cited by examiner

STORAGE CONTAINER AND DISPENSER

CROSS-REFERENCE TO RELATED APPLICATIONS

The present Utility patent application claims priority benefit of the U.S. provisional application for patent Ser. No. 62/807,358 entitled "Storage Container and Dispenser", filed on 19 Feb. 2019, under 35 U.S.C. 119(e). The contents of this related provisional application are incorporated herein by reference for all purposes to the extent that such subject matter is not inconsistent herewith or limiting hereof.

FEDERALLY SPONSORED RESEARCH OR DEVELOPMENT

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND

One or more embodiments of the invention generally relate to storing and dispensing concentrated *cannabis* and other vaporizable concentrate extracted from various plants including hemp, herbs, tobacco and any other semi-solid material that would benefit from the invention such as cosmetics, medicines and chemical compounds. More specifically, the present invention relates to filling a vaporizer cavity that stores a large quantity of concentrate, and to applying a small amount of concentrate onto a vaporizer pen, pipe, other vaping device or any other applicable surface.

The following background information may present examples of specific aspects of the some attempted solutions to the problem associated with vaporizers and pipes (e.g., without limitation, approaches, facts, or common wisdom) that, while expected to be helpful to further educate the reader as to additional aspects of some attempted solutions, is not to be construed as limiting the present invention, or any embodiments thereof, to anything stated or implied therein or inferred thereupon.

Many personal vaporizers and pipes are designed for inhaling the vapor from the solid concentrate derived from plants and herbs. The following is an example of a specific aspect of some attempted solutions to the problem associated with vaporizers and pipes that, while expected to be helpful to further educate the reader as to additional aspects of some attempted solutions to the problem associated with vaporizers and pipes, is not to be construed as limiting the present invention, or any embodiments thereof, to anything stated or implied therein or inferred thereupon.

By way of educational background, another aspect of the prior art generally useful to be aware of is that standard personal vaporizers used for concentrate require manually placing a small amount of the concentrate directly onto an electronic heat source with each use. Pipes also require placing a relatively small amount of concentrate onto a heated bowl which is then vaporized. A third type of personal vaporizer uses a storage chamber that holds a large quantity of concentrate which is then extruded onto the heating element. Unfortunately there are several deficiencies in the methods of applying the concentrate onto or filling it into these devices. More specifically, applying a small amount of concentrate onto a personal vaporizer or pipe incurs a certain amount of mess and waste. This is not the most beneficial and enjoyable experience possible for the consumer. Further, filling a large-capacity chamber can be messy and for the manufacturer, filling containers is a slow and costly process. There are three major deficiencies to some of the attempted solutions for storing and dispensing viscous concentrates.

A deficiency exists with vaporizers and pipes that hold a small amount of extract. A person must use a tool of some sort to separate a small amount of concentrate for loading and then placing the concentrate onto the vaporizer heating element or pipe bowl. The act of regularly placing only a small amount of directly onto the heat source in this manner creates considerable opportunity for waste and hassle. This process creates ample opportunity for spillage and there is waste because some amount of otherwise usable extract always remains on the loading device due to the inherent stickiness of the material. It requires time to go through the process and adding to this, social circumstances are often not conducive to this process.

A second deficiency exists with filling large-capacity chambers because of the sticky, gooey and messy nature of the material being inserted, which makes filling the chamber time consuming, messy and overall, less than ideal. For example, if the material is too soft it is often frozen to make it firmer and easier to insert. Conversely, if it is too hard it must be warmed slightly to make the material more pliable.

A third deficiency exists with filling the common containers used for the packaging and sale of concentrate. Typically, the process is done manually with the result being slow and costly. There exists a need for a container that can be filled using automatic filling machines to speed production, improve accuracy and reduce waste.

In view of the foregoing, it is clear that these traditional techniques are not perfect and leave room for more optimal approaches.

DETAILED DESCRIPTION

The present invention is best understood by reference to the detailed Figures and description set forth herein.

Embodiments of the invention are discussed below with reference to the Figures. However, those skilled in the art will readily appreciate that the detailed description given herein with respect to these Figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settled law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of an object and a rearwardmost point of an object.

Similarly, the term 'substantially' is well recognized in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the Figures thereof, it is improper to rely upon the present written description, the Figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of Claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, are generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. § 112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

As will be described in some detail below with reference to the accompanying Figures, many embodiments of the present invention may provide a high-heat tolerant, FDA or USDA grade, glass tube to store various typical quantities of concentrate and to extrude said concentrate directly onto a vaporizer heating element or pipe or into other types of vaping devices or surfaces. In many embodiments, the extrusion of the concentrate is made controllable with visual markings on the tube to determine the amount of concentrate that has been extruded, which makes the tube easy for an extract manufacturer to fill.

In some other embodiments, a removable cap is provided on each end to seal the tubular storage container. The removable caps may be configured in a manner to also store a plunger component when not in use. A seal may be inserted into the top of the tube before it has been filled with the concentrate. With the end caps detached, one end of the plunger is used to depress the seal and push out the desired amount of concentrate. In many embodiments, a plunger is provided with a visual marking as a secondary means of knowing when the entire amount of concentrate has been transferred into or onto a vaporizer device. In other embodiments, the storage container tube may be straight, or shaped at one end such that it will easily seat inside the opening of the storage chamber of a large-capacity vaporizer device, to allow for the entire amount of concentrate, or a portion thereof, to more easily be pushed from the storage tube into the storage chamber. In some embodiments, a storage container tube stores a significant amount of concentrate while a method is provided for controllably dispensing a desired small amount of the stored concentrate onto or into most types of vaporizing devices to save time, minimize waste and hassle, and eliminate the need for additional tools. In many embodiments, the storage container tube or its components exhibit heat tolerance to prevent melting should components come in contact with heat. In many embodiments, the storage container tube provides safe storage of the concentrate and provides for a more compact and more socially friendly experience. In some other embodiments, considerable cost savings is provided for manufactures using such a device for packaging. The present invention will now be described by referencing the appended Figures representing preferred embodiments.

Figure 1:
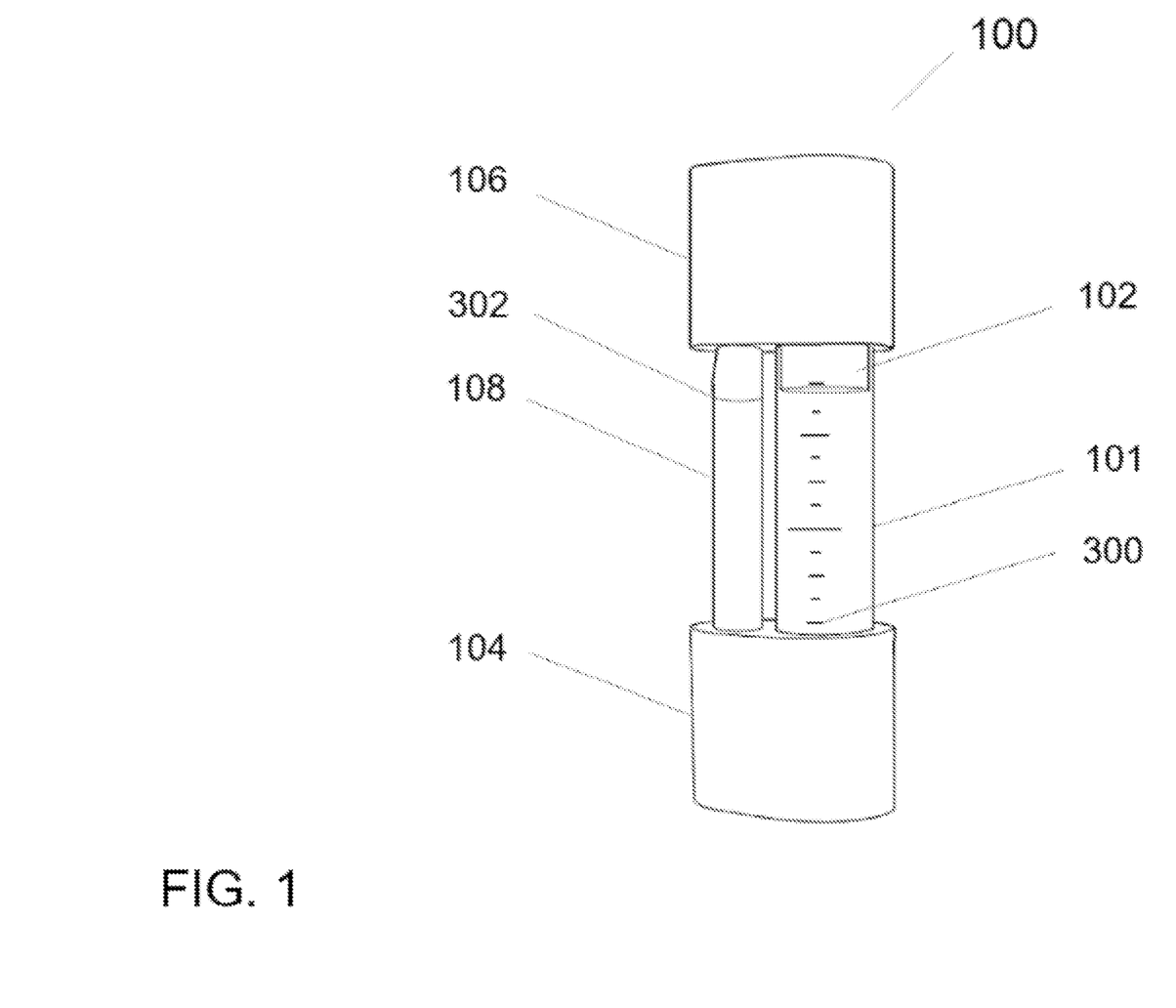
FIG. 1 is a perspective view of an exemplary dispensing mechanism assembly, according to an embodiment of the present invention.

FIG. 1 is a perspective view of an exemplary dispensing mechanism assembly, according to an embodiment of the present invention. In FIG. 1, Concentrate Dispenser 100 is shown in an assembled state. Storage Container Tube 101 holds the concentrate and the Seal 102 is used to extrude the concentrate. Additionally, Plunger 108 is used in part to extrude the concentrate. Storage Container Tube 101 is used to store various typical quantities of concentrate and to extrude said concentrate directly onto a vaporizer heating element or pipe or into other types of vaping devices or surfaces. Caps 104 and 106 seal the ends of Tube 101 and hold Plunger 108 in place. Seal 102 is a flat top and bottom and a snug but not tight fit inside Tube 101.

Bottom Cap 104 is configured to fit tightly over the bottom of Tube 101, and for Top Cap 106 to fit tightly over the top of Tube 101. Plunger 108 is to fit tightly, but not too tight, into Bottom Cap 104 and Top Cap 106 for storage when not in use. Tube 101 includes Markings 300 to indicate the amount of concentrate contained and the amount being extruded. Plunger 108 is to include Marking 302 that is used to indicate when the contents of Tube 101 have been fully expelled.

Tube 101 may be made of high-heat tolerant glass such as quartz or borosilicate, or alternatively it could be made of any other sufficiently rigid and high-heat tolerant material such as titanium or steel. Further, the construction details of the invention are that Seal 102, Top Cap 106 and Bottom Cap 104 are made of silicone because of its flexibility, high-heat tolerance, FDA food-grade standards and resistance to sticking. Alternatively, Seal 102, Top Cap 106 and Bottom Cap 104 may be made all or partially of other flexible material such as plastic or similar materials. Rigid materials such as wood might be used if a flexible material were added to allow sealing to the rigid glass tube, or with threads for use with material where threads can be machined in. Further, Plunger 108 is made from a rigid material such as bamboo for its heat resistance and sustainability. Other embodiments might include wood, metal or plastic.

Figure 2A:
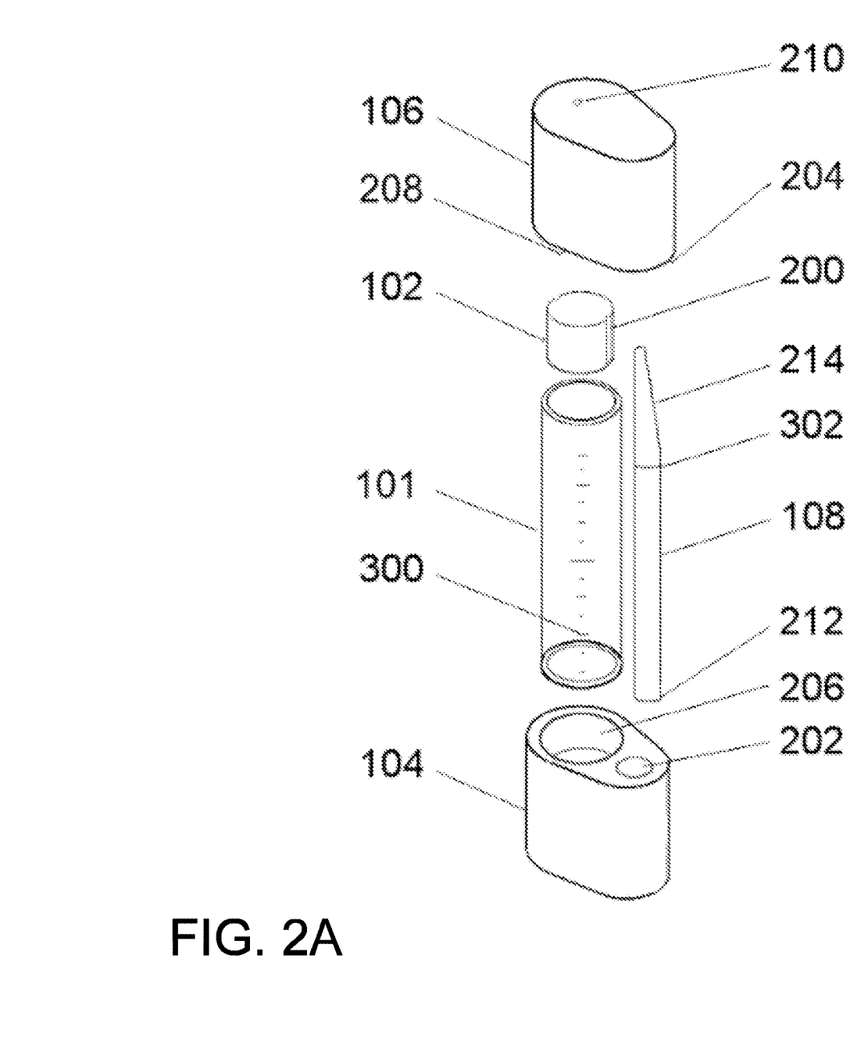
FIG. 2A is an exploded view of the exemplary dispensing mechanism assembly, according to an embodiment of the present invention.

FIG. 2A shows an exploded view of an embodiment of the present invention. The methods of use and description of the invention are as follows. The first step is to insert Seal 102 into the top of Tube 101. The remaining order of assembly is dependent on the process desired by the user; therefore, the specific order can vary. Additionally, the parts may be shipped to the manufacturer partially pre-assembled in a variety of ways. Embodiments of the present invention may therefore be described by referencing two variations of the most common methods of assembly. The first variation involves using an automatic filling machine. The second variation is to use a manual filling machine. Economically and accurately distributing small amounts of concentrate into a container for sale to the end user provides a benefit to manufacturers.

The first variation involves the automatic filling of Tube 101. The top of Tube 101 is positioned top down into a properly sized hole of a filling machine tray with Seal 102 towards the bottom of the filling tray and with the bottom of Tube 101 facing upward. The filling of Tube 101 is then performed. Once Tube 101 is filled, Slot 206 of Bottom Cap 104 is attached over the bottom of Tube 101 and pressed until it is firmly sealed. Tube 101 is then removed from the tray. These steps can be done with capping machinery or manually. Once the partial assembly is removed from the tray, with Plunger Top 214 of Plunger 108 already fully inserted into Slot 204 of Top Cap 106, the top of Tube 101 is then inserted into Slot 208 of Top Cap 106, while simultaneously the round Plunger Bottom 212 of Plunger 108 is inserted into Slot 202 of Bottom Cap 104. The entire embodiment is pressed until the Dispenser and Storage Device 100 is tightly sealed.

The second variation involves the manual filing of Tube 101. In the manual variation, the top of Tube 101 is first inserted into Slot 208 of Top Cap 106. Top Cap 106 is then held manually with the bottom side facing upward. Tube 101 is then filled at the open bottom end, using a manual filling machine. Once Tube 101 is filled, with Plunger Bottom 212 of Plunger 108 already fully inserted into Slot 202 of Bottom Cap 104, the bottom of Tube 101 is inserted into Slot 206 of Bottom Cap 104, while the shaped Plunger Top 214 of Plunger 108 is simultaneously inserted into Slot 204 of Top Cap 106 and the entire embodiment is pressed until the Dispenser and Storage Device 100 is completely sealed.

Figure 2B:
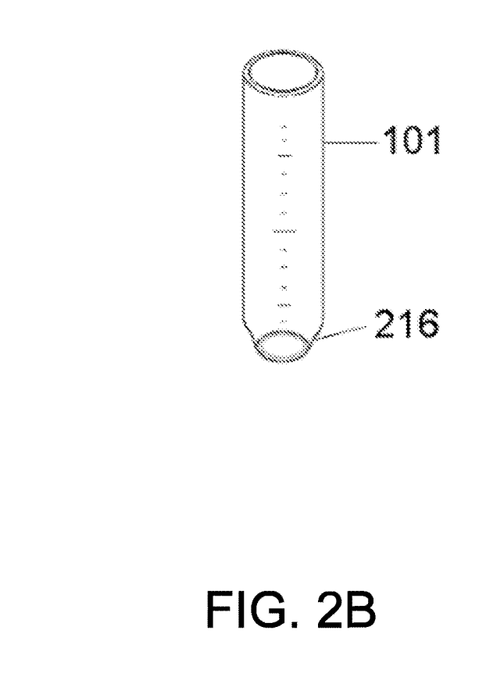
FIG. 2B shows an alternative configuration for the bottom end of a tube to be seated in an exemplary dispensing mechanism assembly, according to an embodiment of the present invention.

FIG. 2B shows an alternative method of forming the bottom end of Tube 101 with a Shape 216, which is for the purpose of seating Tube 101 into the opening of a concentrate storage chamber to achieve more stability and easier gripping for overall easier ejection of the entire contents into the storage chamber.

Storage Container Tube 101 may be straight, or shaped at one end such that it will easily seat inside the opening of the storage chamber of a large-capacity vaporizer device. The shape of Storage Container Tube 101 allows for the entire amount of concentrate, or a portion there of, to more easily be pushed from the Storage Container Tube 101 into a storage chamber of a vaporizer device.

Figure 3:
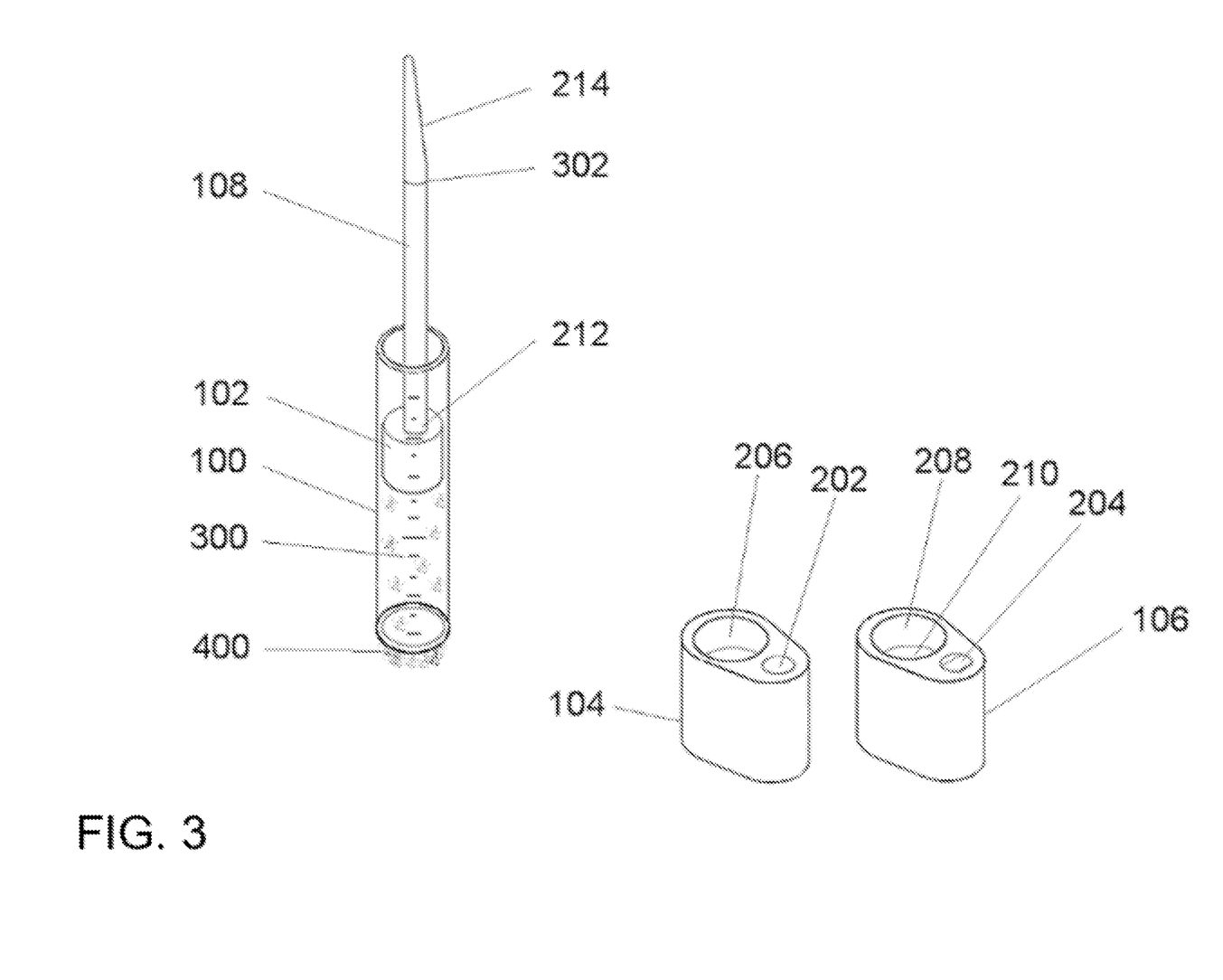
FIG. 3 is a perspective view of the exemplary dispensing mechanism assembly engaged, according to an embodiment of the present invention.

FIG. 3 shows the dispenser in an active state. The invention is comprised of several components that when combined benefits the end user by providing a means to controllably dispense a determined amount of Concentrate 400 from storage Tube 101 for use with any concentrate vaping device, or other similar application. Seal 102 may be inserted into the top of Tube 101 before it has been filled with the concentrate. With Bottom Cap 104 and Top Cap 106 detached, one end of the plunger 108 is used to depress Seal 102 and push out the desired amount of concentrate.

Plunger Bottom 212 of Plunger 108 is configured to have sufficient surface area to easily depress Seal 102. When Plunger 108 is depressed, Concentrate 400 extrudes, in a controlled manner, the desired amount of concentrate, which may be easily wiped onto a vaporizer heating element or onto a pipe bowl or other surface with minimal to zero need of a secondary tool. Further, Plunger Top 214 is shaped in such a manner that it can be used to clean up or manipulate the Concentrate 400 that has been extruded, thereby eliminating the need to carry another tool. Further, Plunger 108 has a Marking 302, which when at the same level of the top of Storage Tube 101, indicates that the total amount of concentrate has been expelled. When Seal 102 is fully depressed, the extrusion of Concentrate 400 is complete.

Figure 4:
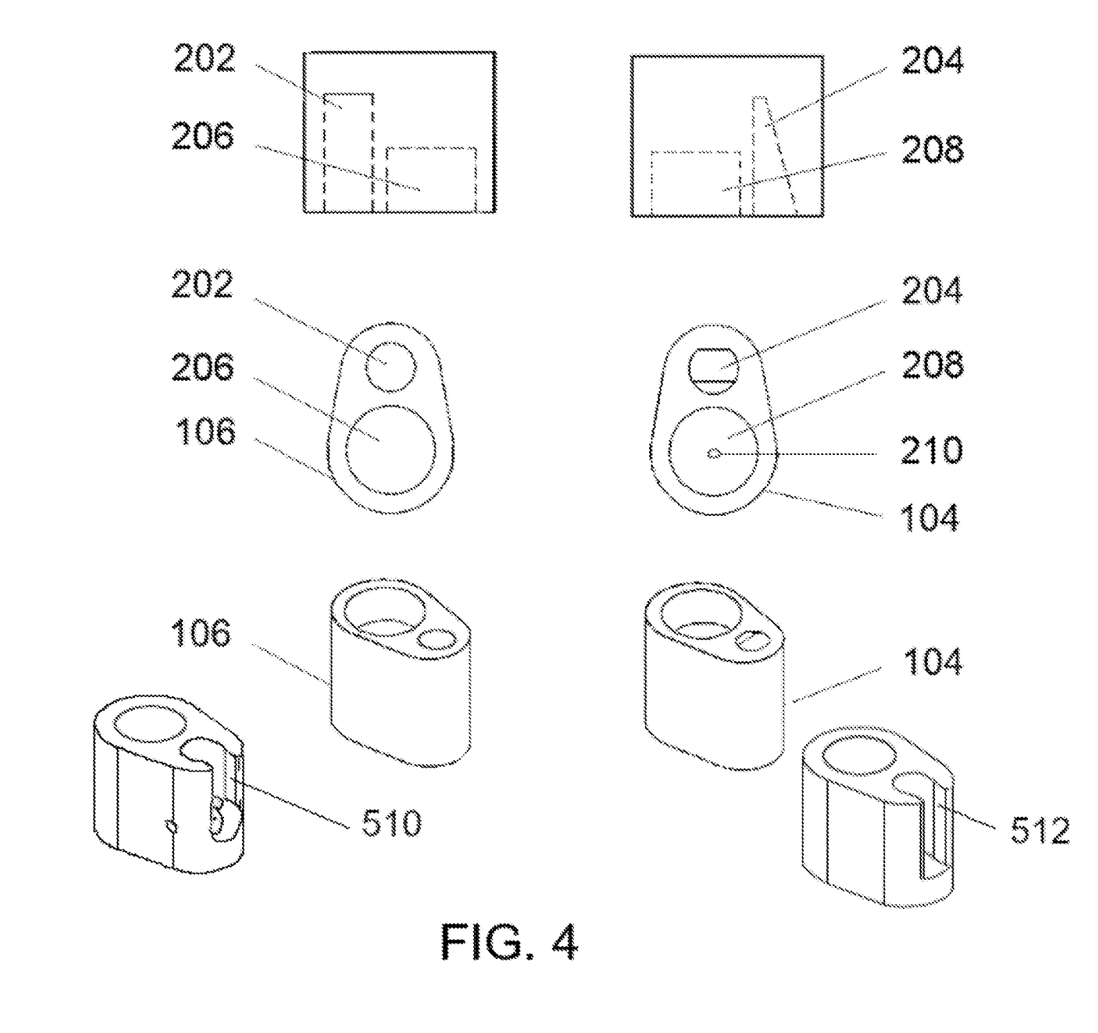
FIG. 4 is a perspective view of the exemplary cap assembly, according to an embodiment of the present invention.

FIG. 4 shows Bottom Cap 104 and Top Cap 106 in a side view, top view and perspective view. The side view drawings show the depth of Cap Holes 206 and 208 that house Tube 101 and the depth of Cap Holes 202 and 204 that house Plunger 108, which are deeper. This allows for Plunger 108 to be longer than Tube 101, which then allows the end user to maintain a sufficient hold on Plunger 108 when Seal 102 is fully depressed and the extrusion of Concentrate 400 is complete. The top view of Top Cap 106 shows Air Vent 210, which is equalizes the airflow to prevent pressurization. Further, Slot 204 is shaped to snugly fit over the shaped Plunger Top 214 of Plunger 108 and the top of Tube 101. The top view of Bottom Cap 104 shows the round shape of Slot 202, which fits snugly over the shape of Plunger Bottom 212 of Plunger 108 and the bottom of Tube 101. Alternatively, Plunger 108 could be attached to the Bottom Cap 104 using a hinge pin assembly 510. The purpose would be a simpler design. Plunger 108 would swing out for use and snap into a Groove 512 in Top Cap 106 when not in use.

Figure 5:
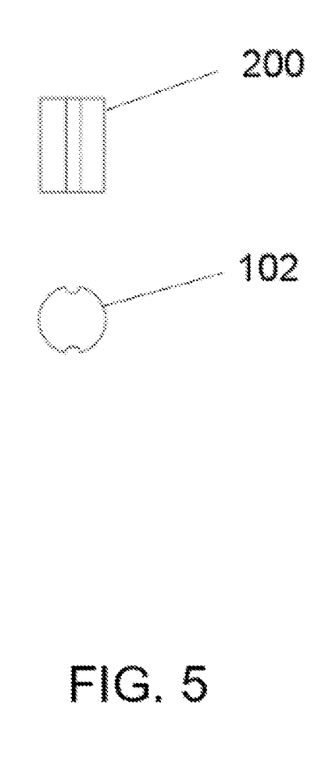
FIG. 5 is a perspective view of the exemplary seal assembly, according to an embodiment of the present invention.

FIG. 5 shows a side and top view of the Seal 102. Seal 102 has small slots 200 to allow air to pass when extruding Concentrate 400, to equalize the airflow to prevent pressurization. Seal 102 is used in part to extrude the concentrate from Storage Container Tube 101, which holds the concentrate. As described earlier, Seal 102, as well as Top Cap 106 and Bottom Cap 104, may be configured using silicone because of its flexibility, high-heat tolerance, FDA food-grade standards and resistance to sticking. Alternatively, Seal 102, as well as Top Cap 106 and Bottom Cap 104, may be made all or partially of other flexible material such as plastic or similar materials. Rigid materials such as wood might be used for Caps 106 and 104 if a flexible material were added to allow sealing to the rigid glass tube, or with threads for use with material where threads can be machined in.

Figure 6A:
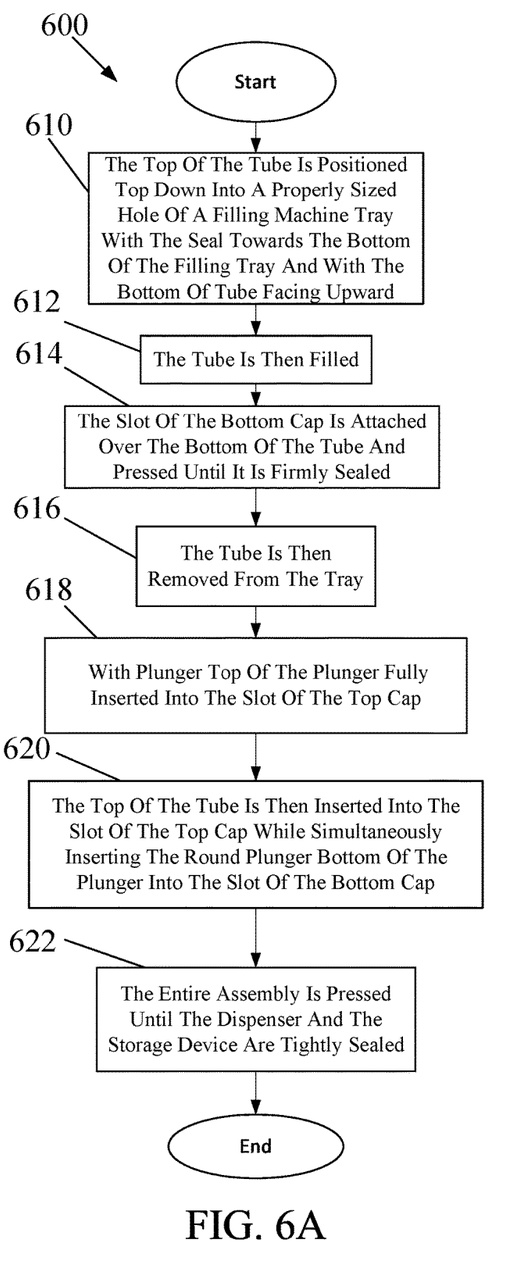
FIG. 6A is a flowchart showing a first exemplary variation involved in the automatic filling of the tube, according to an embodiment of the present invention; and, FIG. 6B is a flowchart showing an exemplary second variation involved in the manual filling of the tube, according to an embodiment of the present invention.

FIG. 6A is a flowchart showing the first variation 600 involved in the automatic filling of the tube. The top of the tube is positioned top down into a properly sized hole of a filling machine tray with the seal towards the bottom of the filling tray and with the bottom of tube facing upward 610. The tube is then filled 612. The slot of the bottom cap is attached over the bottom of the tube and pressed until it is firmly sealed 614. The tube is then removed from the tray 616. With plunger top of the plunger fully inserted into the slot of the top cap 618. The top of the tube is then inserted into the slot of the top cap while simultaneously inserting the round plunger bottom of the plunger into the slot of the bottom cap 620. The entire assembly is pressed until the dispenser and the storage device are tightly sealed 622.

Figure 6B:
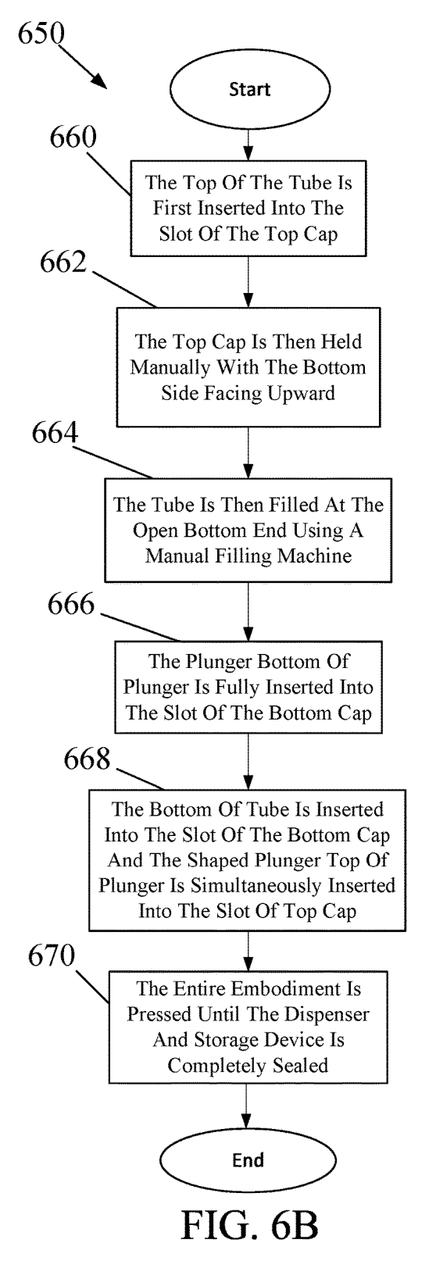

FIG. 6B is a flowchart showing the second variation 650 involved in the manual filling of the tube. The top of the tube is first inserted into the slot of the top cap 660. The top cap is then held manually with the bottom side facing upward 662. The tube is then filled at the open bottom end using a manual filling machine 664. The plunger bottom of plunger is fully inserted into the slot of the bottom cap 666. The bottom of tube is inserted into the slot of the bottom cap and the shaped plunger top of plunger is simultaneously inserted into the slot of top cap 668. The entire embodiment is pressed until the dispenser and storage device is completely sealed 670.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6). In some embodiments, the methods and/or system components which may be located and/or performed remotely include, without limitation: data sources, and interaction with $3^{rd}$ party products.

It is noted that according to USA law, all claims must be set forth as a coherent, cooperating set of limitations that work in functional combination to achieve a useful result as a whole. Accordingly, for any claim having functional limitations interpreted under 35 USC § 112 (6) where the embodiment in question is implemented as a client-server system with a remote server located outside of the USA, each such recited function is intended to mean the function of combining, in a logical manner, the information of that claim limitation with at least one other limitation of the claim. For example, in client-server systems where certain information claimed under 35 USC § 112 (6) is/(are) dependent on one or more remote servers located outside the USA, it is intended that each such recited function under 35 USC § 112 (6) is to be interpreted as the function of the local system receiving the remotely generated information required by a locally implemented claim limitation, wherein the structures and or steps which enable, and breathe life into the expression of such functions claimed under 35 USC § 112 (6) are the corresponding steps and/or means located within the jurisdiction of the USA that receive and deliver that information to the client (e.g., without limitation, client-side processing and transmission networks in the USA). When this application is prosecuted or patented under a jurisdiction other than the USA, then "USA" in the foregoing should be replaced with the pertinent country or countries or legal organization(s) having enforceable patent infringement jurisdiction over the present application, and "35 USC § 112 (6)" should be replaced with the closest corresponding statute in the patent laws of such pertinent country or countries or legal organization(s).

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing a software forecast application system according to the present invention will be apparent to those skilled in the art. Various aspects of the invention have been described above by way of illustration, and the specific embodiments disclosed are not intended to limit the invention to the particular forms disclosed. The particular implementation of the software forecast application system may vary depending upon the particular context or application. By way of example, and not limitation, the software forecast application system described in the foregoing were principally directed to a software application that may be operated on a user's device to provide the user with event predictions based on at least a user's location, wherein events may be particularly related to crime implementations; however, similar techniques may instead be applied to providing weather, sporting, astrological, political, stock market, relationship compatibility, and epidemiology event predictions, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. A device, comprising:
a storage container tube configured to hold a viscous concentrate;
a first cap configured to fit over a first end of the storage container tube;
a second cap configured to fit over a second end of the storage container tube;
in which the first cap and the second cap comprise silicone;
wherein the first cap and the second cap hold the storage container tube in place for storage and seal the viscous concentrate within the storage container tube; and
a plunger configured to be operable for fitting in the first cap and the second cap and hold the plunger in place for storage, the plunger being further configured with an angled end to allow manipulation of the viscous concentrate.

2. The device of claim 1 in which the first cap includes a first slot for fitting over the storage container tube.

3. The device of claim 1 further comprises a seal disposed within the storage container tube, the seal being configured to extrude the viscous concentrate by receiving a force applied with the plunger, the plunger configured to have a surface area to depress the seal when the plunger is depressed within the storage container tube to extrude the viscous concentrate.

4. The device of claim 3 in which the seal comprises a silicone material.

5. The device of claim 1 in which the storage container tube includes markings to indicate the amount of concentrate contained and the amount being extruded, and in which the plunger includes markings to indicate when the contents of storage container tube have been fully expelled.

6. The device of claim 1 in which the second cap comprises: a proximate round slot shaped to fit over the plunger and a top of the storage container tube.

7. The device of claim 1 in which the first cap includes an air vent to allow airflow to prevent pressurization within the storage container tube.

8. The device of claim 1 in which the first cap includes a slot shaped to fit over the plunger and a top of the storage container tube.

9. The device of claim 8 in which the second cap includes a slot to fit over the plunger.

10. The device of claim 1 in which the storage container tube comprises at least one of a quartz, borosilicate, titanium, and steel.

11. The device of claim 1 further comprising:
a seal disposed within the storage container tube, the seal being configured to extrude the viscous concentrate by receiving a force applied with the plunger, the plunger further configured to have a surface area to depress the seal when the plunger is depressed within the storage container tube to extrude the viscous concentrate;
wherein the seal comprises a silicone material, wherein the storage container tube includes markings to indicate the amount of concentrate contained and the amount being extruded, and in which the plunger includes markings to indicate when the contents of the storage container tube have been fully expelled, wherein the first cap includes an air vent to allow airflow to prevent pressurization within the storage container tube, wherein the first cap includes a slot shaped to fit over the plunger and a top of the storage container tube, and wherein the storage container tube comprises a high-heat tolerant material.

12. A device, comprising:
a storage container tube configured to hold a viscous concentrate;
in which the storage container tube being sealed at a first end;
a first cap configured to fit over a second end of the storage container tube;
in which the first cap comprises silicone;
wherein the first cap is further configured to hold the storage container tube in place for storage and seals the viscous concentrate within the storage container tube; and
a second cap configured to fit over the first end of the storage container tube;
in which the second cap comprise silicone; and
a plunger, wherein the plunger being configured to fit the first cap and the second cap and hold the plunger in place for storage, the plunger being further configured with an angled end to allow manipulation of the viscous concentrate.

13. The device of claim 12 in which the first cap comprises a slot to fit over the second end of the storage container tube.

14. The device of claim 12 further comprises a seal disposed within the storage container tube, the seal being configured to extrude the viscous concentrate by receiving a force applied with the plunger, the plunger configured to have a surface area to depress the seal when the plunger is depressed within the storage container tube to extrude the viscous concentrate.

15. The device of claim 14 in which the seal comprises a silicone material, and in which the first cap includes an air vent to allow airflow to prevent pressurization within the storage container tube.

16. The device of claim 12 in which the first cap includes a slot shaped to fit over the plunger and a top of the storage container tube.

17. The device of claim 12 in which the storage container tube comprises at least one of a quartz, borosilicate, titanium, and steel.

18. A device, comprises:
means for holding a viscous concentrate;
a first capping means that is configured to be operable for fitting over a first end of the holding means;
a second capping means that is configured to be operable for fitting over a second end of the holding means;
in which the first capping means and the second capping means comprise silicone;
wherein the first capping means and the second capping means is further configured to hold the holding means in place for storage and seal the viscous concentrate within the holding means; and
means for applying a force and means for sealing the holding means, wherein the sealing means disposed within the holding means, and wherein the sealing means being configured to extrude the viscous concentrate by receiving a force applied with the force applying means.

19. The device of claim 18 further comprises means for receiving the force applying means; and
means for receiving the holding means.

20. The device of claim 18 in which the first capping means includes an air vent to allow airflow to prevent pressurization within the holding means, the force applying means and the holding means being held in place for storage.

* * * * *